United States Patent
Smith et al.

(10) Patent No.: US 7,951,118 B2
(45) Date of Patent: May 31, 2011

(54) INTRODUCER SEAL ASSEMBLY

(75) Inventors: Robert C. Smith, Cheshire, CT (US);
David C. Racenet, Litchfield, CT (US);
Gene A. Stellon, Southington, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/613,816

(22) Filed: Nov. 6, 2009

(65) Prior Publication Data

US 2010/0049138 A1    Feb. 25, 2010

Related U.S. Application Data

(63) Continuation of application No. 11/069,098, filed on Mar. 1, 2005, now Pat. No. 7,632,250, which is a continuation-in-part of application No. 10/264,556, filed on Oct. 4, 2002, now abandoned.

(60) Provisional application No. 60/379,651, filed on May 10, 2002, now abandoned.

(51) Int. Cl.
*A61M 5/178* (2006.01)
*A61B 17/32* (2006.01)

(52) U.S. Cl. ......... 604/167.01; 604/167.02; 604/167.06; 606/167

(58) Field of Classification Search ......... 604/167.01–167.06, 164.08; 606/167
See application file for complete search history.

(56) References Cited

U.S. PATENT DOCUMENTS

| | | | |
|---|---|---|---|
| 3,421,509 A | 1/1969 | Fiore | |
| 3,565,078 A | 2/1971 | Vailliancourt et al. | |
| 3,853,127 A | 12/1974 | Spademan | |
| 3,907,310 A | 9/1975 | Dufour | |
| 3,994,287 A | 11/1976 | Turp et al. | |
| 4,000,739 A | 1/1977 | Stevens | |
| 4,112,932 A | 9/1978 | Chiulli | |
| 4,173,350 A | 11/1979 | Sieghartner | |
| 4,177,814 A | 12/1979 | Knepshield et al. | |
| 4,177,997 A | 12/1979 | Cartwright | |
| 4,240,335 A | 12/1980 | Stucka et al. | |
| 4,240,411 A | 12/1980 | Hosono | |
| 4,311,315 A | 1/1982 | Kronenberg | |
| 4,334,688 A | 6/1982 | Spargo et al. | |

(Continued)

FOREIGN PATENT DOCUMENTS

DE       1893771       5/1964

(Continued)

OTHER PUBLICATIONS

European Search Report for EP 09015886.6-1269.5-1269 date of completion is Feb. 5, 2010 (3 pages).

(Continued)

*Primary Examiner* — Nicholas D Lucchesi
*Assistant Examiner* — Ian K Holloway

(57) ABSTRACT

A seal assembly for use with an access device includes a seal housing defining a central longitudinal axis, an inner wall and an outer wall. The inner wall defines a longitudinal opening to permit passage of instrumentation through the seal housing. A gimbal mount is at least partially accommodated within a space defined between the inner wall and the outer wall of the seal housing. The gimbal mount includes a seal member defining an aperture for substantial sealed reception of a surgical instrument. The gimbal mount is adapted for angular movement relative to the central longitudinal axis upon angulation of the surgical instrument while substantially maintaining the sealed reception of the surgical instrument.

22 Claims, 8 Drawing Sheets

U.S. PATENT DOCUMENTS

| | | |
|---|---|---|
| 4,338,689 A | 7/1982 | Zieg |
| 4,383,692 A | 5/1983 | Proctor |
| 4,386,756 A | 6/1983 | Muchow |
| 4,387,879 A | 6/1983 | Tauschinski |
| 4,430,081 A | 2/1984 | Timmermans |
| 4,447,237 A | 5/1984 | Frisch et al. |
| 4,448,449 A | 5/1984 | Halling et al. |
| 4,464,178 A | 8/1984 | Dalton |
| 4,553,760 A | 11/1985 | Reed et al. |
| 4,588,195 A | 5/1986 | Antonini et al. |
| 4,601,710 A | 7/1986 | Moll |
| 4,626,245 A | 12/1986 | Weinstein |
| 4,641,842 A | 2/1987 | Kataoka |
| 4,654,030 A | 3/1987 | Moll et al. |
| 4,655,752 A | 4/1987 | Honkanen et al. |
| 4,673,393 A | 6/1987 | Suzuki et al. |
| 4,705,511 A | 11/1987 | Kocak |
| 4,715,360 A | 12/1987 | Akui et al. |
| 4,723,550 A | 2/1988 | Bales et al. |
| 4,758,225 A | 7/1988 | Cox et al. |
| 4,842,591 A | 6/1989 | Luther |
| 4,844,483 A | 7/1989 | Iijima et al. |
| 4,844,484 A | 7/1989 | Antonini et al. |
| 4,857,062 A | 8/1989 | Russell |
| 4,869,717 A | 9/1989 | Adair |
| 4,889,349 A | 12/1989 | Muller |
| 4,909,798 A | 3/1990 | Fleischhacker et al. |
| 4,912,287 A | 3/1990 | Ono et al. |
| 4,932,633 A | 6/1990 | Johnson et al. |
| 4,943,280 A | 7/1990 | Lander |
| 4,966,588 A | 10/1990 | Rayman et al. |
| 4,998,740 A | 3/1991 | Tellier |
| 5,000,745 A | 3/1991 | Guest et al. |
| 5,002,557 A | 3/1991 | Hasson |
| 5,015,000 A | 5/1991 | Perini |
| 5,038,756 A | 8/1991 | Kepley |
| 5,041,095 A | 8/1991 | Littrell |
| 5,053,014 A | 10/1991 | Van Heugten |
| 5,053,016 A | 10/1991 | Lander |
| 5,073,169 A | 12/1991 | Raiken |
| 5,104,383 A | 4/1992 | Schicman |
| 5,123,634 A | 6/1992 | Schwerdt |
| 5,137,520 A | 8/1992 | Maxson et al. |
| 5,167,636 A | 12/1992 | Clement |
| 5,180,373 A | 1/1993 | Green et al. |
| 5,209,737 A | 5/1993 | Ritchart et al. |
| 5,211,370 A | 5/1993 | Powers |
| 5,226,891 A | 7/1993 | Bushatz et al. |
| 5,273,545 A | 12/1993 | Hunt et al. |
| 5,290,304 A | 3/1994 | Storace |
| 5,299,813 A | 4/1994 | McKenna |
| 5,300,036 A | 4/1994 | Mueller et al. |
| 5,342,315 A | 8/1994 | Rowe et al. |
| 5,385,553 A | 1/1995 | Hart et al. |
| 5,499,823 A | 3/1996 | Fukui |
| 5,603,702 A | 2/1997 | Smith et al. |
| 5,613,954 A | 3/1997 | Nelson et al. |
| 5,685,854 A | 11/1997 | Green et al. |
| 5,720,759 A * | 2/1998 | Green et al. ............... 606/167 |
| 5,779,697 A | 7/1998 | Glowa et al. |
| 5,792,113 A * | 8/1998 | Kramer et al. ........... 604/167.01 |
| 5,820,600 A * | 10/1998 | Carlson et al. .......... 604/167.03 |
| 5,839,639 A | 11/1998 | Sauer et al. |
| 6,039,725 A | 3/2000 | Moenning et al. |
| RE36,702 E * | 5/2000 | Green et al. ............... 606/167 |
| 6,086,603 A | 7/2000 | Termin et al. |
| 6,113,106 A | 9/2000 | Dahlheimer |
| 6,231,565 B1 | 5/2001 | Tovey et al. |
| 6,942,671 B1 * | 9/2005 | Smith ......................... 606/108 |
| 2004/0059297 A1 * | 3/2004 | Racenet et al. ......... 604/167.06 |
| 2004/0066008 A1 | 4/2004 | Smith |
| 2004/0204682 A1 * | 10/2004 | Smith ..................... 604/167.06 |
| 2006/0161049 A1 * | 7/2006 | Beane et al. ............... 600/207 |

FOREIGN PATENT DOCUMENTS

| | | |
|---|---|---|
| DE | 3217118 | 8/1983 |
| EP | 0029864 | 6/1981 |
| EP | 0051718 | 5/1982 |
| EP | 0113520 | 7/1984 |
| EP | 0312219 | 4/1989 |
| EP | 1 707 133 | 10/2006 |
| GB | 1482857 | 8/1977 |
| GB | 2298905 | 9/1996 |
| WO | WO 93 04717 | 3/1993 |
| WO | WO 97/42991 | 11/1997 |
| WO | WO 98/53865 | 12/1998 |
| WO | WO 98 53865 | 12/1998 |
| WO | WO 02/41795 | 5/2002 |
| WO | WO 03/94760 | 11/2003 |

OTHER PUBLICATIONS

U.S. Appl. No. 09/706,643, filed Nov. 6, 2000.

* cited by examiner

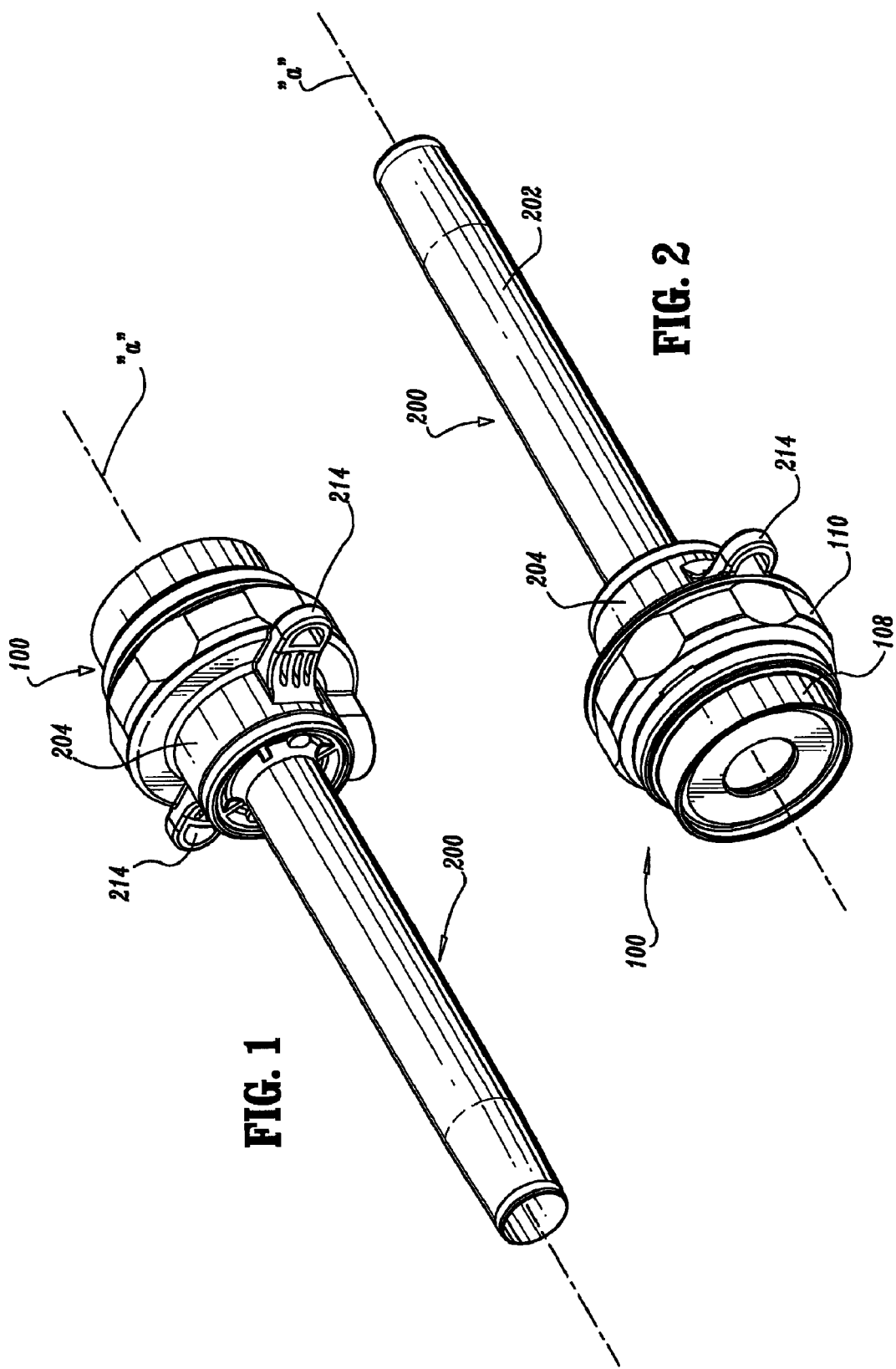

INTRODUCER SEAL ASSEMBLY

CROSS REFERENCE TO RELATED APPLICATIONS

The present application is a continuation of U.S. application Ser. No. 11/069,098 filed Mar. 1, 2005, now U.S. Pat. No. 7,632,250 which is a continuation-in-part of U.S. patent application Ser. No. 10/264,556 filed on Oct. 4, 2002, now abandoned, which claims the benefit of and priority to U.S. Provisional Application Serial No. 60/379,651 filed on May 10, 2002, now abandoned. The disclosures of which are hereby incorporated by reference in its entirety.

BACKGROUND

1. Technical Field

The present disclosure relates to valve system adapted to permit the introduction of surgical instrumentation into a patient's body. In particular, the present disclosure relates to a valve system for use with an introducer which is intended for insertion into a patient's body, and to receive an instrument in sealing engagement therewith.

2. Description of the Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere. In view of the need to maintain the atmospheric integrity of the inner area of the cavity, a seal assembly for a cannula, which permits introduction of a wide range of surgical instrumentation and maintains the atmospheric integrity of the inner area of the cavity is desirable. In this regard, there have been a number of attempts in the prior art to achieve such sealing requirements. A difficulty encountered with conventional seal assemblies, however, is the inability of accommodating the wide range of sizes of instrumentation. In addition, angulation and/or manipulation of instrumentation within the cannula often present difficulties with respect to maintaining seal integrity.

SUMMARY

Accordingly, the present disclosure provides a seal assembly which will allow a surgeon to efficaciously utilize instruments of varying diameter in a surgical procedure. This seal assembly obviates the need for multiple adapters to accommodate instruments of varying diameter by providing an apertured resilient seal member which is mounted in a gimbal-like assembly, thereby facilitating alignment of the instrument with the aperture of the seal member.

In a preferred embodiment, a seal assembly for use with an access device includes a seal housing defining a central longitudinal axis. The seal housing includes an inner wall and an outer wall. The inner wall defines a longitudinal opening to permit passage of instrumentation through the seal housing. A gimbal mount is at least partially accommodated within a space defined between the inner wall and the outer wall of the seal housing. The gimbal mount includes a seal member defining an aperture for substantial sealed reception of a surgical instrument. The gimbal mount is adapted for angular movement relative to the central longitudinal axis upon angulation of the surgical instrument while substantially maintaining the sealed reception of the surgical instrument. The gimbal mount preferably defines a general hemispherical configuration.

The seal housing may include a skirt seal which is positioned adjacent the gimbal mount and adapted to minimize passage of fluids through the seal housing. The skirt seal may extend to contact the gimbal mount, and bias the gimbal mount in a general proximal direction. The skirt seal is dimensioned and configured to bias the gimbal mount against the inner wall of the seal housing. Preferably, the inner wall of the seal housing defines a distal arcuate surface in contacting relation with a corresponding inner arcuate surface of the gimbal mount.

The preferred seal member includes a resilient member and a protective layer juxtaposed relative to the resilient member. The protective layer of the seal member extends at least partially within the aperture to protect portions of the seal member defining the aperture during passage of the surgical instrument. The protective layer may include a fabric material.

The seal housing is adapted to be detachably mounted to a cannula assembly for providing a substantially fluid-tight seal when the instrument is inserted into the seal assembly and through the cannula assembly.

In an alternate embodiment, the seal assembly for use with an access device includes a seal housing defining a central longitudinal axis and having proximal and distal ends. The seal housing includes an inner wall defining an opening to permit passage of instrumentation through the seal housing. A gimbal mount is disposed within the seal housing. The gimbal mount is adapted for angular movement within the seal housing about an axis of rotation. The gimbal mount includes a seal defining an aperture for sealed reception of a surgical instrument. A skirt member is engageable with a peripheral portion of the gimbal mount, and is dimensioned to bias the gimbal mount in a proximal direction against the seal housing. The seal housing defines a distal angulating surface which is in contacting relation with the gimbal mount. Preferably, the gimbal mount defines an interior surface corresponding to the distal angulating surface of the seal housing, and in contacting relation therewith. The interior surface traverses the distal angulating surface upon angular movement of the gimbal mount. The gimbal mount may also define a general hemispherical configuration.

In another embodiment, the seal assembly for use with an access device includes a seal housing defining a central longitudinal axis and a longitudinal passageway for permitting passage of a surgical instrument, and a generally hemispherical seal element disposed within the seal housing. The seal element defines a seal axis and an aperture for sealed reception of the surgical instrument. The seal element is adapted for angular movement within the seal housing to accommodate angular movement of the surgical instrument whereby the seal axis intersects the central longitudinal axis of the seal housing.

The seal assembly is adapted to be associated with a cannula assembly. The cannula assembly typically includes a tubular cannula and a cannula housing within which is positioned a cannula seal assembly. The cannula seal assembly typically provides structure which is adapted to provide a fluid-tight seal in the absence of a surgical instrument. Suitable cannula seal assemblies include a spring loaded flapper valve, a trumpet valve, a duck bill valve, or the like. The seal assembly of the invention may be associated with the cannula housing by any suitable means, e.g., a bayonet lock.

In use, the seal assembly may be associated with a cannula assembly at any point the surgeon desires flexibility in the instrument sizes he may utilize therethrough. Thus, for example, if the surgeon is utilizing a 15 mm cannula assembly in an endoscopic surgical procedure and determines that it would be advantageous to have the flexibility to use instruments ranging in size from 5 to 15 mm through that cannula assembly, the seal assembly may be secured to the cannula assembly. Thereafter, instruments ranging in diameter from 5 to 15 mm may be efficaciously introduced therethrough. The cylindrical guide wall guides the instrument toward the aperture of the resilient seal member. The gimbal mount angularly repositions itself with respect to the housing in response to the manipulation of the instrument.

The movement of the gimbal mount relative to the housing which is accommodated by the gimbal-like structure also facilitates seal maintenance once an instrument is being used within the body cavity. In particular, as an instrument is manipulated, the resilient seal member moves through movement of the gimbal mount relative to the housing, thereby ensuring that the resilient seal member maintains a fluid-tight seal around the instrument shaft.

BRIEF DESCRIPTION OF THE DRAWINGS

The foregoing features of the present disclosure will become more readily apparent and will be better understood by referring to the following detailed description of preferred embodiments, which are described hereinbelow with reference to the drawings wherein:

FIGS. 1-2 are perspective views of a cannula assembly and a seal assembly in accordance with the principles of the present disclosure;

DETAILED DESCRIPTION OF PREFERRED EMBODIMENTS

Figure 3:
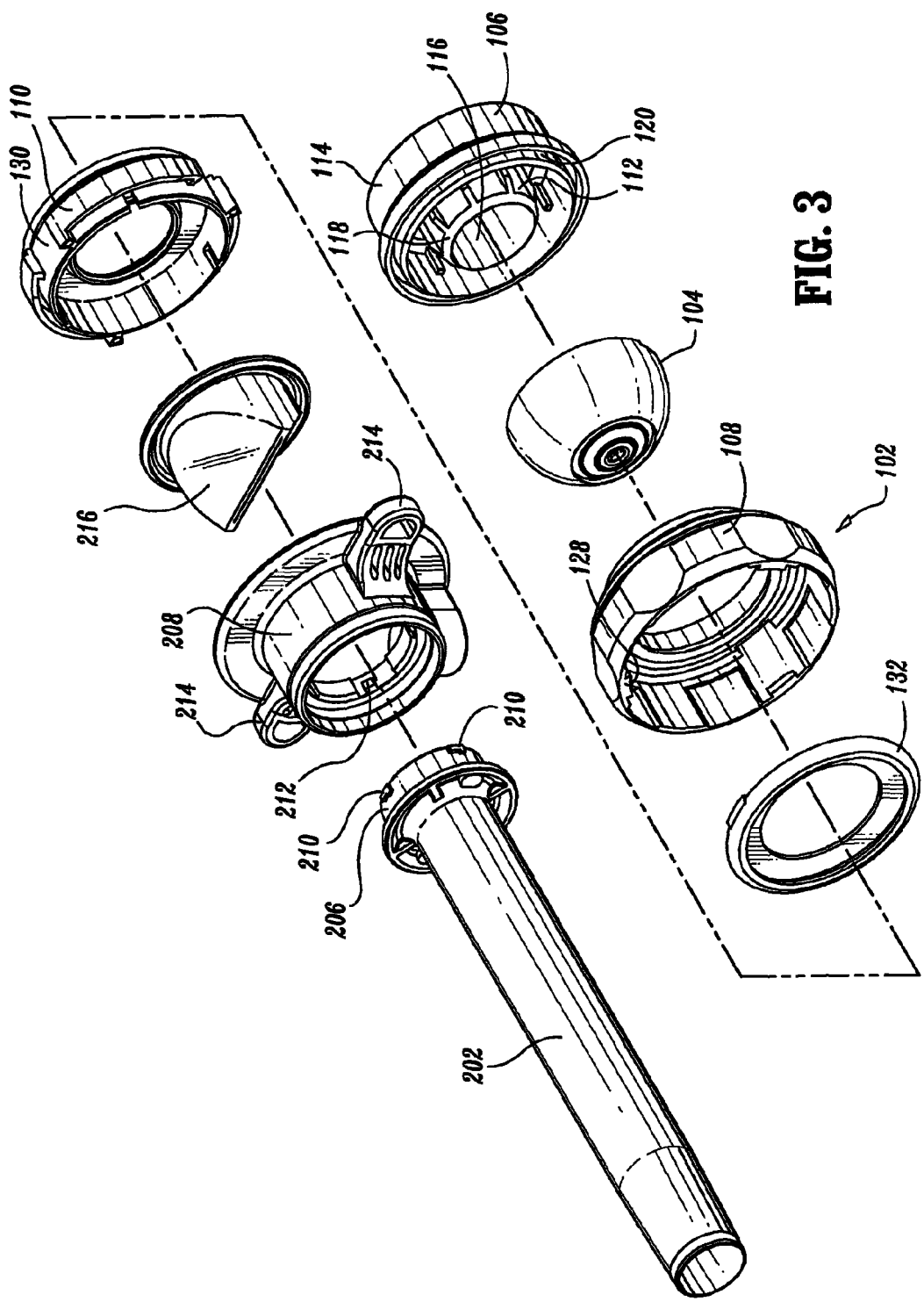
FIG. 3 is a perspective view with parts separated of the cannula and seal assemblies of FIG. 1.

The seal assembly of the present disclosure, either alone or in combination with a seal system internal to a cannula assembly, provides a substantial seal between a body cavity of a patient and the outside atmosphere before, during and after insertion of an instrument through the cannula assembly. Moreover, the seal assembly of the present invention is capable of accommodating instruments of varying diameters, e.g., from 5 mm to 15 mm, by providing a gas tight seal with each instrument when inserted. The flexibility of the present seal assembly greatly facilitates endoscopic surgery where a variety of instruments having differing diameters are often needed during a single surgical procedure.

The seal assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Specifically, the seal assembly accommodates angular manipulation of the surgical instrument relative to the seal axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laproscopes, tubes, and the like. Such instruments will be collectively referred to herein as "instruments or instrumentation".

In the following description, as is traditional the term "proximal" refers to the portion of the instrument closest to the operator while the term "distal" refers to the portion of the instrument remote from the operator.

Referring now to the drawings, in which like reference numerals identify identical or substantially similar parts throughout the several views, FIGS. 1-2 illustrate the seal assembly 100 of the present disclosure mounted to cannula assembly 200. Cannula assembly 200 may be any conventional cannula suitable for the intended purpose of accessing a body cavity and permit introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown) which is a sharp pointed instrument positionable within the passageway of the cannula assembly 200. The obturator assembly is utilized to penetrate the abdominal wall and then subsequently removed from the cannula assembly to permit introduction of the surgical instrumentation utilized to perform the procedure.

Cannula assembly 200 includes cannula sleeve 202 and cannula housing 204 mounted to an end/of the sleeve 202. Cannula sleeve 202 defines a longitudinal axis "a" extending along the length of sleeve 202. Sleeve 202 further defines an internal longitudinal passage dimensioned to permit passage of surgical instrumentation. Sleeve 202 may be formed of stainless steel or other rigid materials such as a polymeric material or the like. Sleeve 202 may be clear or opaque. The diameter of sleeve 202 may vary, but typically ranges from 10 to 15 mm for use with the seal assembly 100 of the present disclosure.

Figure 4:
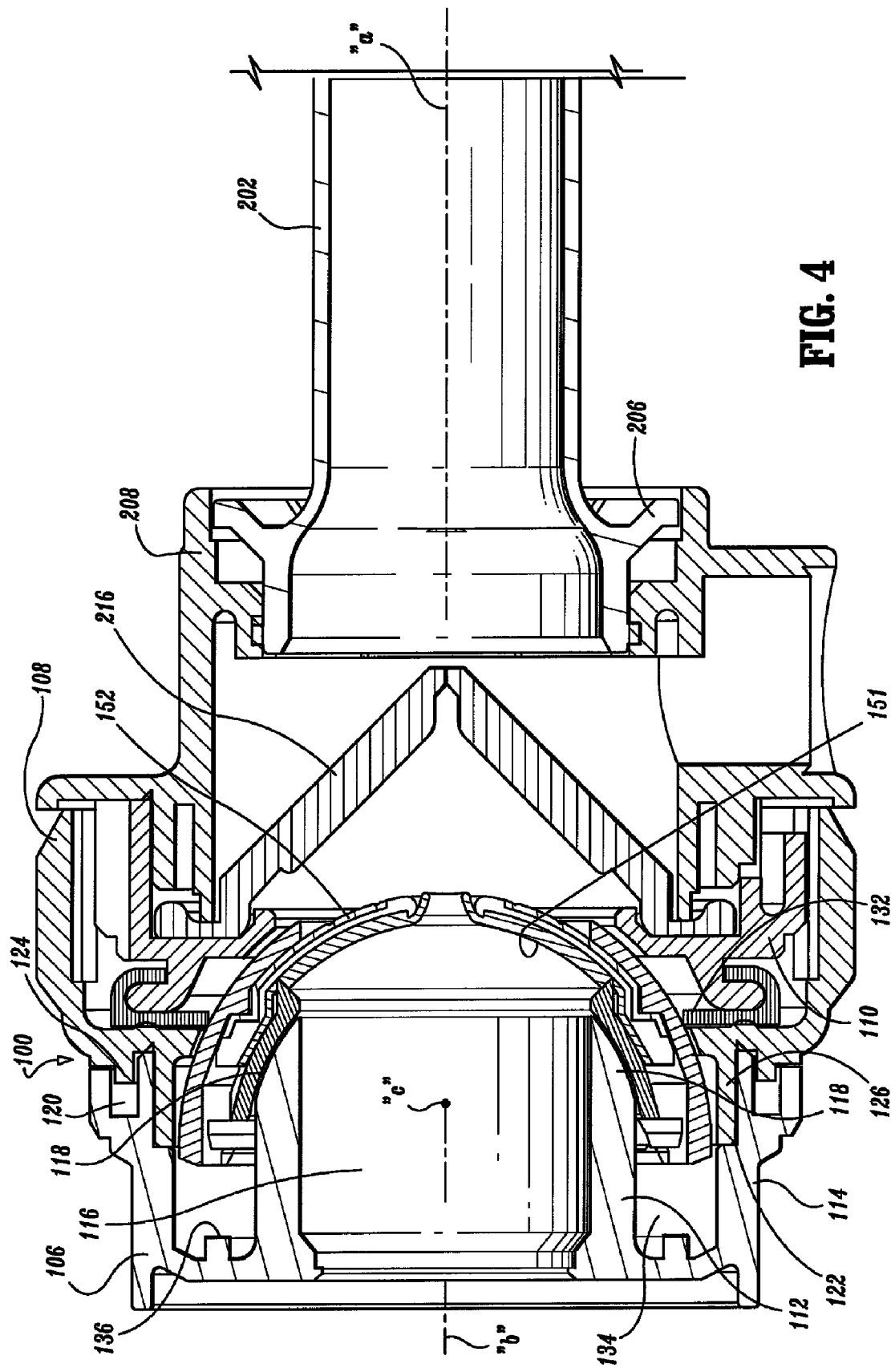
FIG. 4 is a side cross-sectional view of the cannula and seal assemblies.
Figure 7:
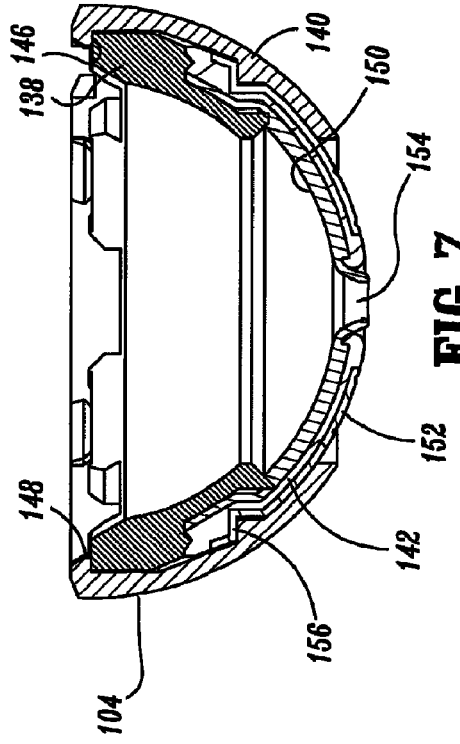
FIGS. 7-8 are cross-sectional views of the gimbal mount.
Figure 8:
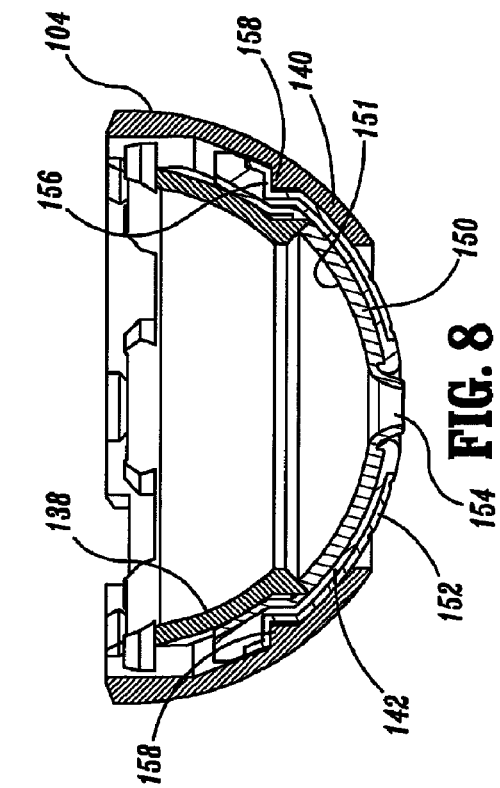
Figure 5:
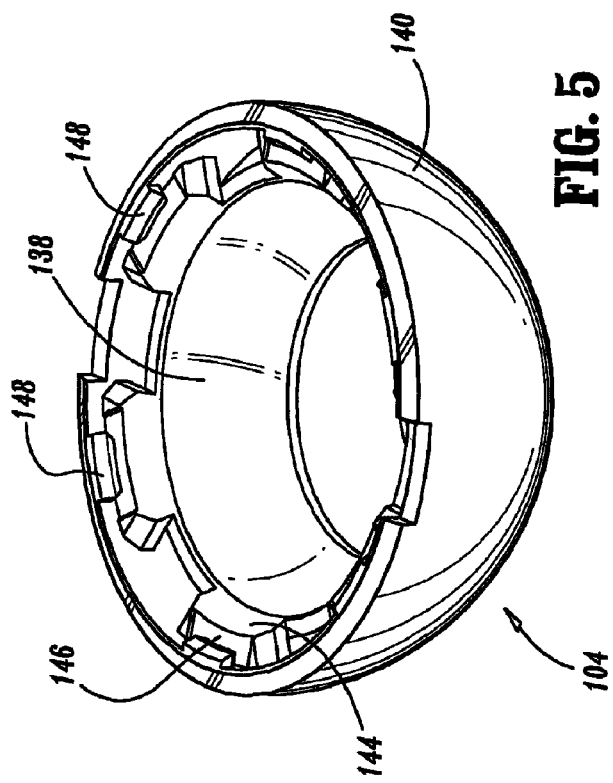
FIGS. 5-6 are top and bottom perspective views of the gimbal mount of the seal assembly.

Cannula housing 204 includes two components, specifically, housing flange 206 which is attached to the proximal end of cannula sleeve 202 and main housing 208 as shown in FIGS. 3-4. Main housing 208 is connectable to housing flange 206 through a bayonet coupling consisting of radially spaced tongues 210 on the exterior of housing flange 206 and corresponding recesses 212 within the interior of main housing 208. Tongues 210 are receivable within recesses 212. Thereafter, housing flange 206 and main housing 208 are rotated to securely lock the tongues 210 within the recesses 212. Other conventional means, e.g., a snap fit, ultrasonic welding or any other means envisioned by one skilled in the art including, e.g., adhesive means, may be incorporated to connect housing flange 206 and main housing 208. Main housing 208 further includes diametrically opposed housing grips 214 dimensioned and arranged for gripping engagement by the fingers of the user. Although shown and described as two components, cannula housing 204 may be a single component and attached to cannula sleeve 202 by any of the aforementioned means.

With reference to FIG. 3, in conjunction with FIGS. 1-2, cannula housing 204 further includes duck bill or zero closure valve 216 which tapers distally and inwardly to a sealed configuration as shown in the figure. Valve 216 opens to permit passage of the surgical instrumentation and closes in the absence of the instrumentation. Valve 216 is preferably adapted to close upon exposure to the forces exerted by the insufflation gases in the internal cavity. Other zero closure valves are also contemplated including single or multiple slit valve arrangements, trumpet valves, flapper valves, etc.

Referring now to FIGS. 3-4, in conjunction with FIGS. 1-2, seal assembly 100 will be discussed in detail. Seal assembly 100 includes seal housing, generally identified as reference numeral 102, and gimbal mount 104 which is disposed within the seal housing 102. Seal housing 102 houses the sealing components of the assembly and defines the outer valve or seal body of the seal assembly 100. Seal housing 102 defines central seal housing axis "b" which is preferably parallel to the axis "a" of cannula sleeve 202 and, more specifically, coincident with the axis "a" of the cannula. Seal housing 102 incorporates three housing components, namely, proximal, distal and inner housing components 106, 108, 110, respectively, which, when assembled together, form the seal housing 102. Assembly of housing components 106, 108, 110 may be affected by any of the aforementioned connection means discussed with respect to cannula housing 204. Further, seal housing 102 may be considered as having an upper housing portion 109 formed by components 106 108, as shown separately in FIGS. 10-12, and a detachable lower housing portion formed by component 110.

Proximal housing component 106 defines inner guide wall 112 and outer wall 114 disposed radially outwardly of the inner guide wall 112. Inner guide wall 112 defines central passage 116 which is dimensioned to receive a surgical instrument and laterally confine the instrument within seal housing 102. Inner guide wall 112 is generally cylindrical in configuration and terminates in a distal arcuate surface 118. Outer wall 114 defines first and second annular recesses 120, 122 adjacent its distal end. Recesses 120, 122 receive corresponding structure, e.g., annular lips 124, 126 of distal housing component 108 to facilitate connection of the two components. As appreciated, proximal housing component 106 may also incorporate locking tabs which engage corresponding structure of distal housing component 108 upon relative rotation of the components 106, 108 to securely connect the components.

Inner housing component 110 is disposed within the interior of distal housing component 108 and securely connectable to the distal housing component 108 through a bayonet coupling. Such coupling includes radially spaced tongues 128 which depend radially inwardly to be received within correspondingly arranged grooves or recesses 130 on the exterior of inner housing component 110. Coupling of distal and inner housing components 108, 110 is thereby affected through simple rotation of the components.

With continued reference to FIGS. 3 and 4, seal assembly 100 further includes skirt seal 132 mounted about the proximal end of inner housing component 110 or on the upper surface of the inner housing component (constituting a lower component) of the seal housing. Skirt seal 132 functions in minimizing the loss of insufflation gases through seal assembly 102. Skirt seal 132 also engages gimbal mount 104 and serves to bias the gimbal mount in a proximal direction against inner guide wall 112 of proximal housing 106 as will be discussed. Skirt seal 132 is preferably fabricated from a suitable elastomeric material or the like to provide a spring-like characteristic sufficient to appropriately bias gimbal mount 104.

With particular reference to FIG. 4, gimbal mount 104 is accommodated within an annular space 134 defined between inner and outer walls 112, 114 of proximal housing component 106. Gimbal mount 104 is mounted in a mariner which permits angulation of the gimbal mount 104 relative to seal axis "b". Specifically, gimbal mount 104 is free to angulate about an axis or center of rotation "c" through a range of motion defined within the confines of annular space 134. An annular stop 136 may extend within annular space 134. Annular stop 136 is positioned to limit the degree of angulation of gimbal mount 104 if desired. The range of movement of gimbal mount 104 will be discussed in greater detail hereinbelow.

Referring now to FIGS. 5-9, in conjunction with FIG. 4, the components of gimbal mount 104 will be discussed in further detail. Gimbal mount 104 includes first and second gimbal housings 138, 140 and resilient seal member 142 which is mounted between the housings 138, 140. In a preferred arrangement, first and second gimbal housings 138, 140 and seal member 142 each define a general hemispherical configuration as shown. First gimbal housing 138 is preferably seated within second gimbal housing 140 and secured to the second gimbal housing 140 through a snap fit connection or the like. Preferably, first gimbal housing 138 includes a plurality of mounting legs 144 radially spaced about the outer periphery of the housing component 134. Legs 144 define locking surfaces 146 which extend in general transverse relation to the axis "b" of seal assembly 200. Similarly, second gimbal housing 140 includes a plurality of corresponding locking detents 148 spaced about the interior of the housing 140. Upon insertion of first gimbal housing 138 within second gimbal housing 140, mounting legs 144 slide along locking detents 148 whereby upon clearing the detents 148, locking surfaces 146 of the mounting legs 146 securely engage the locking detents 148 to fix first gimbal housing 138 within second gimbal housing 140 and securing resilient seal member 142 between the components in sandwiched relation. As appreciated, first gimbal housing 138 may be sufficiently resilient to deflect upon insertion to permit mounting legs 144 to clear locking detents 148 and return to their initial position to engage the detents 148.

As mentioned hereinabove, seal member 142 of gimbal mount 104 is secured in interposed relation between first and second gimbal housings 138, 140. Seal member 142 preferably comprises a resilient center material (e.g., polyisoprene or natural rubber) with first and second layers of fabric 150, 152 impregnated on the respective proximal and distal surfaces of the resilient center material. Fabric may be of any suitable fabric for example, a SPANDEX material containing about 20% LYCRA and about 80% NYLON available from Milliken. A suitable seal member or seal type is disclosed in commonly assigned U.S. patent application Ser. No. 09/449, 368, filed Nov. 24, 1999, the contents of which are incorporated herein by reference. Seal member 142 defines central aperture 154 for sealed reception of a surgical instrument. In a preferred arrangement, first layer 150 is arranged to extend or overlap into aperture 154. In this manner, the fabric (which is stronger relative to the resilient material) is positioned to engage the surgical instrument upon passage through aperture 154 of seal member 142 thereby protecting the resilient material defining the aperture. This advantageously minimizes the potential of piercing, penetrating or tearing of the resilient material by the instrument. Alternatively, an additional layer of fabric 151 on the proximal surface of seal member 142 may be superposed and arranged to drape within aperture 154. Seal member 142 includes an annular depression 156 on its distal surface, i.e., within second layer 152 of fabric. Depression 156 receives ledge 158 of second gimbal housing 140 to facilitate fixation of seal member 142 between first and second gimbal housings 138, 140.

Figure 6:
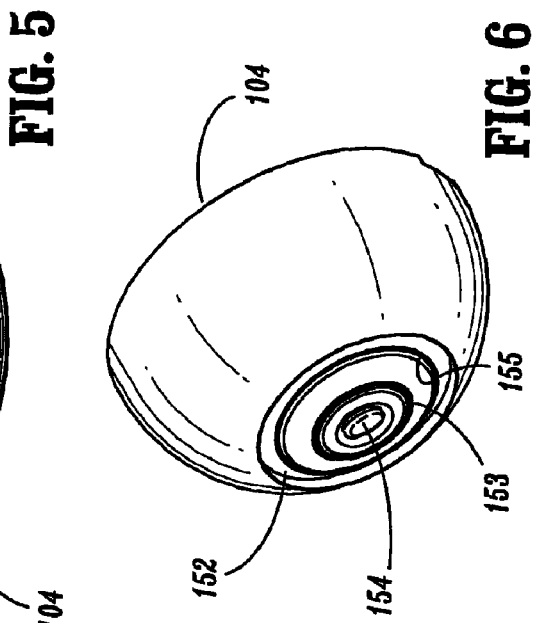
Figure 9:
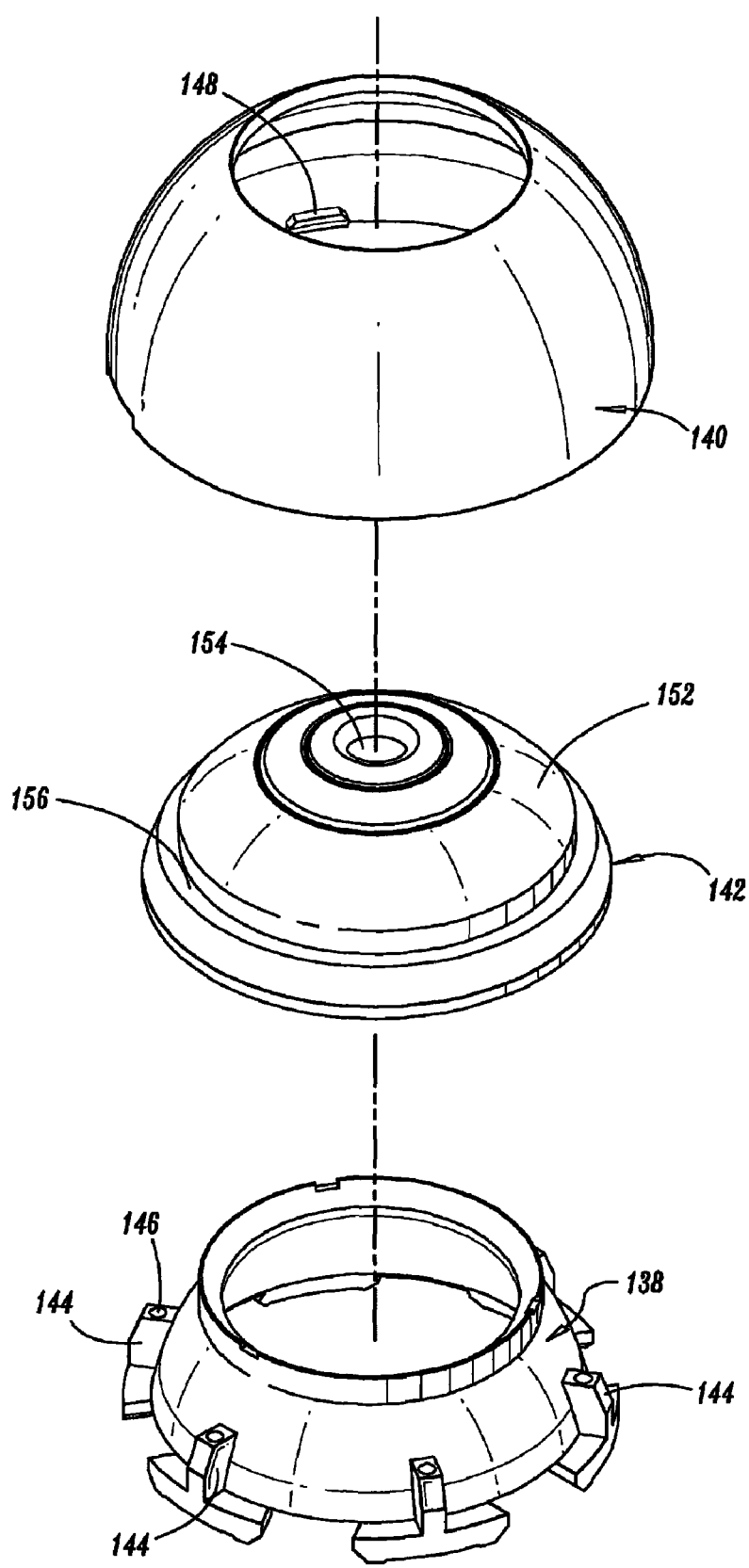
FIG. 9 is a perspective view illustrating the components of the gimbal mount.

Although seal member 142 is disclosed as an impregnated fabric arrangement, it is appreciated that other seal types may be used and still achieve the objectives of the present disclosure. Further, FIG. 6 illustrates annular depressions 153, 155 which have been pressed by a molding tool into layer 153. One or more similar depressions may be pressed into layer 150 to assist positioning of fabric during manufacture of seal member 142.

Figure 12:
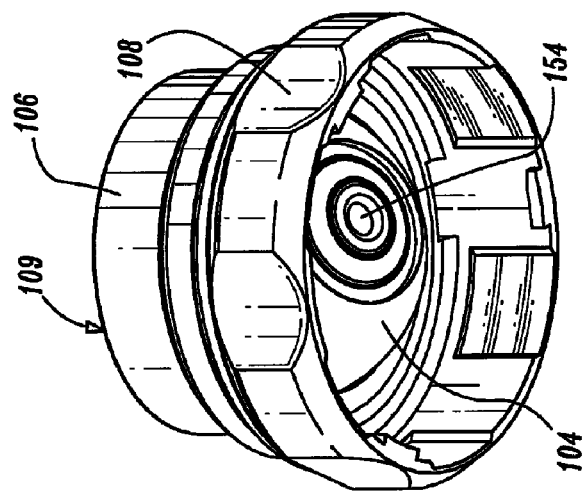
FIGS. 10-12 are perspective views illustrating the range of movement of the gimbal mount within the seal housing.
Figure 11:
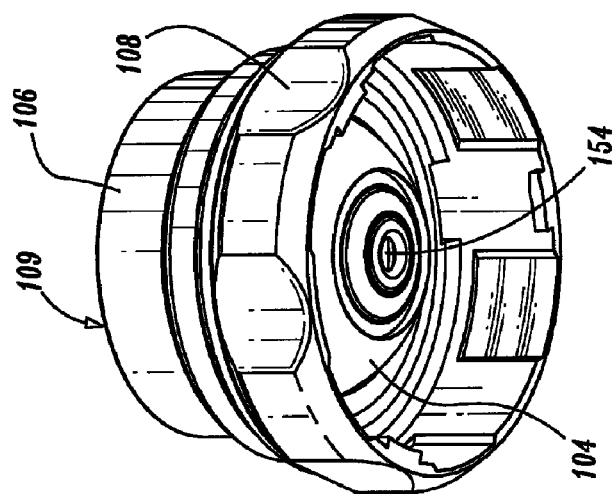
Figure 10:
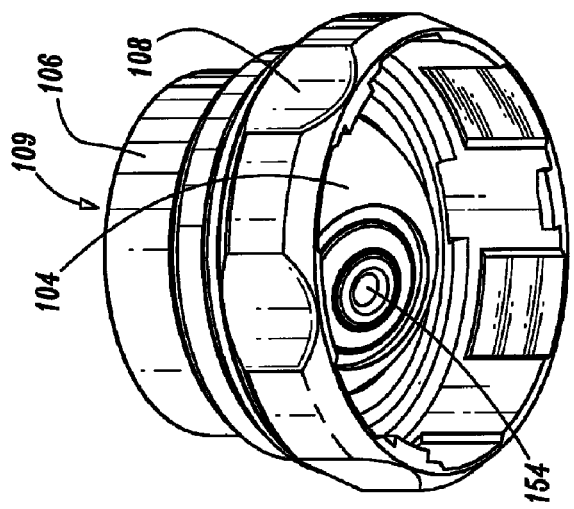

With reference now to FIGS. 10-12, in conjunction with FIG. 4, gimbal mount 104 is free to move within the annular space 134 defined between inner and outer walls 112,114 to permit angulation of the instrument relative to the seal axis "b" while still maintaining a seal thereabout. Specifically, gimbal mount 104 is adapted for swiveling movement about a center of rotation "c" which is coincident with the axis of seal assembly 100. In this regard, the axis of the aperture 154 of seal member 142 intersects the axis "b" of the seal assembly 100 during angulation of the instrument. During angulation, gimbal mount 104 is only in contact with seal housing 102 along distal arcuate surface 118 of proximal housing 106 as well as along skirt seal 132. Specifically, the arcuate inner surface of first gimbal housing 138 rides along distal arcuate surface 118 of inner wall 112 in contacting relation therewith (under the bearing influence of skirt seal 132) to permit gimbal mount 104 to swivel within seal housing 102. Preferably, there is no other contact of gimbal mount 104 with any of the other components of seal housing, which thereby substantially minimizes resistance to the angulating movement. A lubricant may be provided between distal arcuate surface 118 and the inner surface of first gimbal housing 138 to facilitate angulation.

In a preferred arrangement, gimbal mount 104 may angulate or rotate through an angle inclusive of about 25°, more preferably about 22.5° relative to seal axis "b". Annular stop 136 may further restrict angulation by a couple of degrees of movement to be inclusive of an angle of about 19° relative to axis "b".

Seal assembly 100 may be associated with, or joined to, cannula assembly 200 in a variety of ways. In a preferred embodiment, seal housing 102 of seal assembly 100 and cannula housing 204 of cannula assembly 200 are adapted to detachably engage each other, e.g., through a bayonet lock or like mechanical means. As previously discussed, proximal and distal housing components 106, 108 may define an upper housing component 109 which is mountable directly to cannula assembly 200. Alternatively, inner housing portion 110 which defines a lower housing component may be directly mounted to cannula assembly 200 independent of the upper housing component 109. Specifically, the lower housing component 110 which houses gimbal mount 104 may be mounted to cannula assembly independent of the remaining housing components. The upper housing may then be mounted to lower housing or cannula assembly 200 as needed. Even further, upper housing component 109 may be mounted to cannula assembly 200 without lower housing component 110. Other means of joining seal assembly 100 to cannula assembly 200 will be readily apparent to one of ordinary skill in the art.

Figure 13:
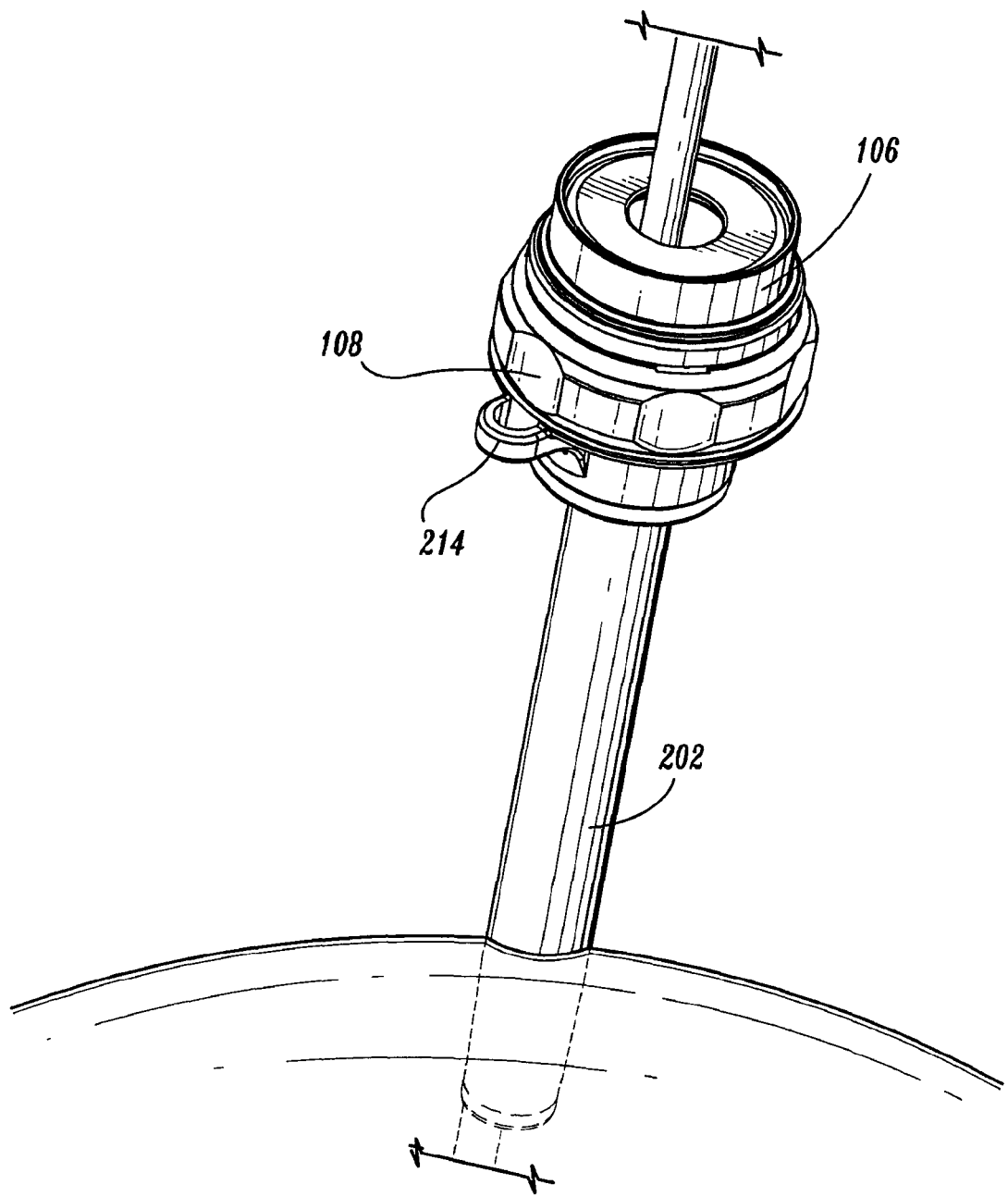
FIG. 13 is a view illustrating the cannula assembly and seal assembly accessing an internal cavity with an instrument introduced therein.
Figure 14:
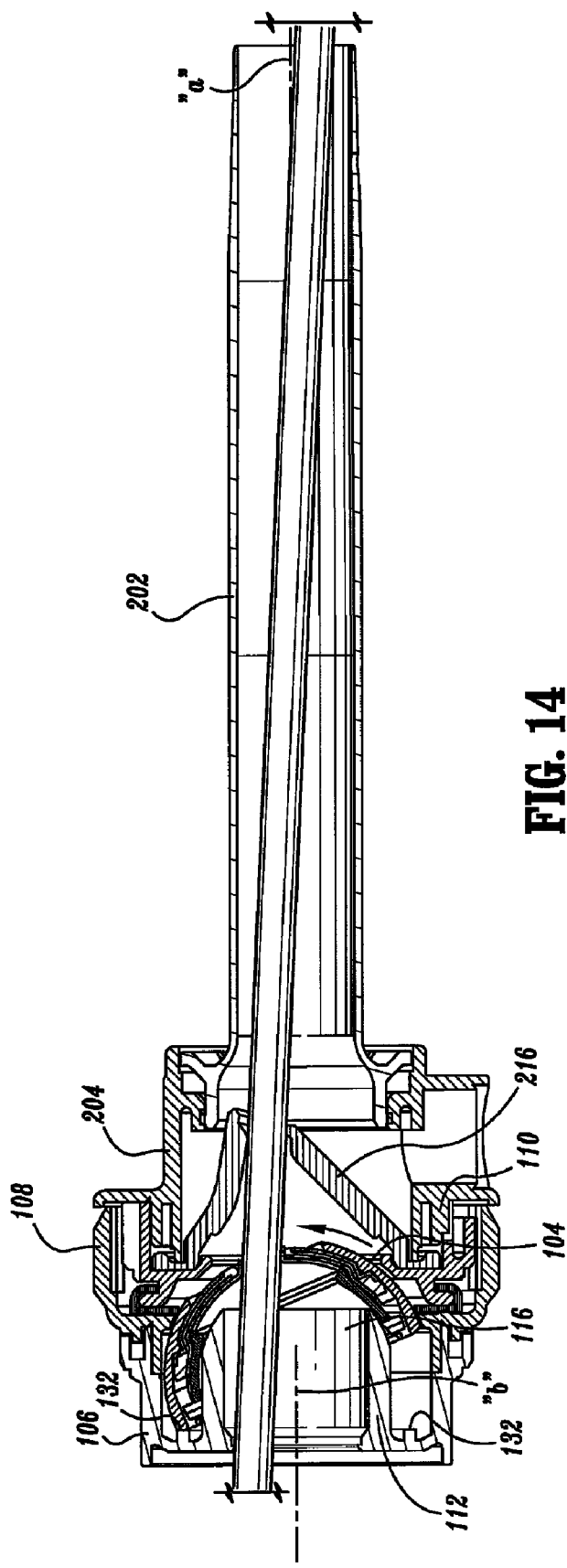
FIG. 14 is a side cross-sectional view of the cannula and seal assemblies illustrating a range of movement of the surgical instrument.

Referring now to FIGS. 13-14, use of the seal assembly 100 and cannula assembly 200 in connection with introduction of a surgical instrument will be discussed. Seal assembly 100 is mounted to cannula assembly 200 which is previously introduced into an insufflated abdominal cavity. An instrument is inserted into seal assembly 100 through passage 116 of inner cylindrical guide wall 112 in seal housing 102. If the axis of the instrument is not perfectly aligned with the axis "a" of cannula assembly 200 or axis "b" of seal assembly 100, then the surgical instrument will contact the inner guide wall 112 and/or the inner surface of seal member 142. Contact with the seal member 142 can cause some deformation of the seal member 142. The instrument slides along the surface of the gimbal mount 104 and/or the seal member 142, to the aperture 154. Aperture 154 stretches to accommodate the instrument diameter, as necessary. The instrument passes further distally into the cannula housing 204 passing through duckbill valve 216 and cannula sleeve 202 into the body cavity. Once the instrument is disposed within the aperture 154, and the friction at the skirt seal 132, gimbal mount 104 and arcuate surface 118 is overcome, gimbal mount 104 swivels with respect to seal housing 102 as the instrument is manipulated. The gimbal mount 104 is free to swivel relative to housing 102, while allowing seal member 142 to maintain sealing engagement with the instrument passed therethrough, as well as maintaining the seal around the gimbal mount 104. Preferably, the seal member 142 includes resilient material and fabric material which resists deformation of the aperture 154, as well as tearing of the seal member 142.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A seal assembly for use with an access device, the seal assembly comprising:
   a seal housing defining a central longitudinal axis and having proximal and distal ends, the seal housing including an inner wall defining an opening to permit passage of instrumentation through the seal housing; and
   a gimbal mount disposed within the seal housing, the gimbal mount adapted for angular movement within the seal housing about an axis of rotation, the gimbal mount comprising:
      a seal defining an aperture for sealed reception of a surgical instrument; and
      a skirt seal engageable with as peripheral portion of the gimbal mount, the skirt seal being dimensioned to bias the gimbal mount in a proximal direction against an arcuate surface of the seal housing, wherein the skirt seal is adapted to minimize passage of fluids through the seal housing, wherein the skirt seal is positioned about the gimbal mount and arranged to establish a frictional relation between the skirt seal, the gimbal mount and the arcuate surface of the seal housing such that manipulation of the instrumentation will cause the frictional relation to be overcome thereby permitting the gimbal mount to swivel with respect to the seal housing.

2. The seal assembly according to claim 1, wherein the seal member includes a resilient member and a protective layer juxtaposed relative to the resilient member.

3. The seal assembly according to claim 2, wherein the protective layer of the seal member extends at least partially within the aperture to protect portions of the seal member defining the aperture during passage of the surgical instrument.

4. The seal assembly according to claim 2, wherein the protective layer includes a fabric material.

5. The seal assembly according to claim 1, wherein the gimbal mount defines a general hemispherical configuration.

6. The seal assembly according to claim 1, wherein the seal assembly includes an upper housing portion and a lower housing portion, and wherein the skirt seal is disposed in mechanical cooperation with the lower housing portion.

7. The seal assembly according to claim 1, wherein the seal housing is disposed in mechanical cooperation with a cannula assembly.

8. A cannula assembly comprising:
   a cannula housing;
   a cannula sleeve extending distally from the cannula housing; and
   a seal assembly disposed in mechanical cooperation with the cannula housing, the seal assembly comprising:
      a seal housing defining a central longitudinal axis, the seal housing including an inner wall integrally connected to an outer wall, the inner wall defining a longitudinal opening to permit passage of instrumentation through the seal housing; and
      a gimbal mount at least partially accommodated within a space defined between the inner wall and the outer wall of the seal housing, the gimbal mount configured for reception of a seal member, the gimbal mount adapted for angular movement relative to the central longitudinal axis upon angulation of the surgical instrument.

9. The cannula assembly according to claim 8, wherein the seal housing includes a skirt seal, the skirt seal positioned about the gimbal mount and adapted to minimize passage of fluids through the seal housing.

10. The cannula assembly according to claim 9, wherein the skirt seal extends to contact the gimbal mount, the skirt seal being adapted to bias the gimbal mount in a general proximal direction.

11. The cannula assembly according to claim 10, wherein the skirt seal is dimensioned and configured to bias the gimbal mount against a portion of the inner wall of the seal housing.

12. The cannula assembly according to claim 11, wherein the inner wall of the seal housing defines a distal arcuate surface in contacting relation with a corresponding inner arcuate surface of the gimbal mount.

13. The cannula assembly according to claim 8, wherein the seal housing is adapted to be detachably mounted to the cannula housing for providing a substantially fluid-tight seal when said instrument is inserted into the seal assembly and through the cannula housing.

14. The cannula assembly according to claim 8, wherein the gimbal mount defines a general hemispherical configuration.

15. A cannula assembly comprising:
   a cannula housing;
   a cannula sleeve extending distally from the cannula housing; and
   a seal assembly disposed in mechanical cooperation with the cannula housing, the seal assembly comprising:
      a seal housing defining a central longitudinal axis and having proximal and distal ends, the seal housing including an inner wall defining an opening to permit passage of instrumentation through the seal housing;
      a gimbal mount disposed within the seal housing, the gimbal mount adapted for angular movement within the seal housing about an axis of rotation, the gimbal mount configured for reception of a seal; and
      a skirt member engageable with a peripheral portion of the gimbal mount, the skirt member dimensioned to bias the gimbal mount in a proximal direction against the seal housing.

16. The cannula assembly according to claim 15, wherein the seal housing defines a distal angulating surface, the distal angulating surface in contacting relation with the gimbal mount.

17. The cannula assembly according to claim 16, wherein the gimbal mount defines an interior surface corresponding to the distal angulating surface of the seal housing and in contacting relation therewith, the interior surface traversing the distal angulating surface upon angular movement of the gimbal mount.

18. The cannula assembly according to claim 15, wherein the gimbal mount defines a general hemispherical configuration.

19. The cannula assembly according to claim 15, wherein the seal assembly includes an upper housing portion and a lower housing portion, and wherein the skirt member is associated with the lower housing portion.

20. The cannula assembly according to claim 15, wherein the gimbal mount is positioned within a space defined between the inner wall and an outer wall of the seal housing such that the gimbal mount is movable relative to the seal housing.

21. The seal assembly according to claim 1, wherein the skirt seal includes an inner circumferential edge that slidingly engages the gimbal mount.

22. The seal assembly according to claim 1, wherein the gimbal mount is rotatable about the central longitudinal axis independently of the skirt seal.

* * * * *